US 11,161,914 B2

(12) United States Patent
Liu et al.

(10) Patent No.: US 11,161,914 B2
(45) Date of Patent: Nov. 2, 2021

(54) HUMAN-DERIVED INSECTICIDAL BT CRY TOXIN MIMETIC, AND DESIGN METHOD AND APPLICATION THEREOF

(71) Applicant: Jiangsu Academy of Agricultural Sciences, Nanjing (CN)

(72) Inventors: Xianjin Liu, Jiangsu (CN); Yajing Xie, Jiangsu (CN); Chongxin Xu, Jiangsu (CN); Xiao Zhang, Jiangsu (CN); Meijing Gao, Jiangsu (CN); Xin He, Jiangsu (CN); Yuan Liu, Jiangsu (CN); Cunzheng Zhang, Jiangsu (CN)

(73) Assignee: Jiangsu Academy of Agricultural Sciences, Jiangsu (CN)

( * ) Notice: Subject to any disclaimer, the term of this patent is extended or adjusted under 35 U.S.C. 154(b) by 0 days.

(21) Appl. No.: 16/535,296

(22) Filed: Aug. 8, 2019

(65) Prior Publication Data
US 2020/0095336 A1    Mar. 26, 2020

(30) Foreign Application Priority Data
Aug. 9, 2018    (CN) .......................... 201810903129.1

(51) Int. Cl.
*A01N 63/10*    (2020.01)
*C07K 16/42*    (2006.01)

(52) U.S. Cl.
CPC .......... *C07K 16/4233* (2013.01); *A01N 63/10* (2020.01); *C07K 2317/14* (2013.01); *C07K 2317/24* (2013.01); *C07K 2317/565* (2013.01); *C07K 2317/622* (2013.01)

(58) Field of Classification Search
CPC ................................................ C07K 16/4233
USPC ....................................................... 800/279
See application file for complete search history.

(56) References Cited

U.S. PATENT DOCUMENTS
9,751,952 B2    9/2017  Liu et al.

FOREIGN PATENT DOCUMENTS
WO    WO-2004081026 A2 *    9/2004    ........... C07K 16/468

OTHER PUBLICATIONS

M. Sullivan et al "Anti-idiotypic monobodies for immune response profiling", Methods 58 (2012) pp. 62-68.
C. Xu et al "Selection and application of broad-specificity human domain antibody for simultaneous detection of Bt Cry toxins", Analytical Biochemistry 512 (2016) pp. 70-77.

* cited by examiner

*Primary Examiner* — Li Zheng
(74) *Attorney, Agent, or Firm* — Harness, Dickey & Pierce, P.L.C.

(57) ABSTRACT

The present invention provides a human-derived molecularly modified insecticidal protein, and a preparation method and application thereof, and belongs to the field of genetic engineering and biological control. The present invention provides a human-derived molecularly modified insecticidal protein, and the amino acid sequence of the insecticidal protein CCL-CCL_scFv is shown as SEQ ID No. 1. The insecticidal protein CCL-CCL_scFv shows significantly higher affinity with midgut BBMV of *Plutella xylostella* than Cry1Ab toxin, competes with Cry1Ab and Cry1Ac toxins for binding the midgut BBMV of *Plutella xylostella*, and is a mimic of Cry1Ab and Cry1Ac toxins. Through *Plutella xylostella* indoor insecticidal biological activity assay, the insecticidal protein shows a good insecticidal effect, and can effectively replace Cry1Ac or Cry1Ab toxin for biological control of insect pest.

4 Claims, 8 Drawing Sheets

Specification includes a Sequence Listing.

B12_scFv  
FIG. 2A

CCL-CCL_scFv  
FIG. 2B

CCH-CCH_scFv  
FIG. 2C

Cry1Ab  
FIG. 2D

PxALP  
FIG. 2E

FIG. 4

FIG. 5A
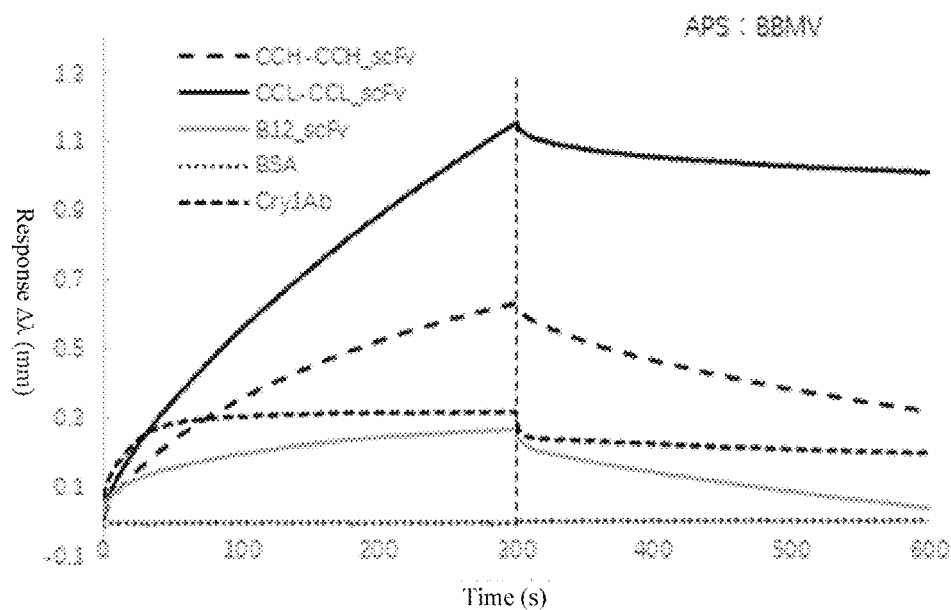
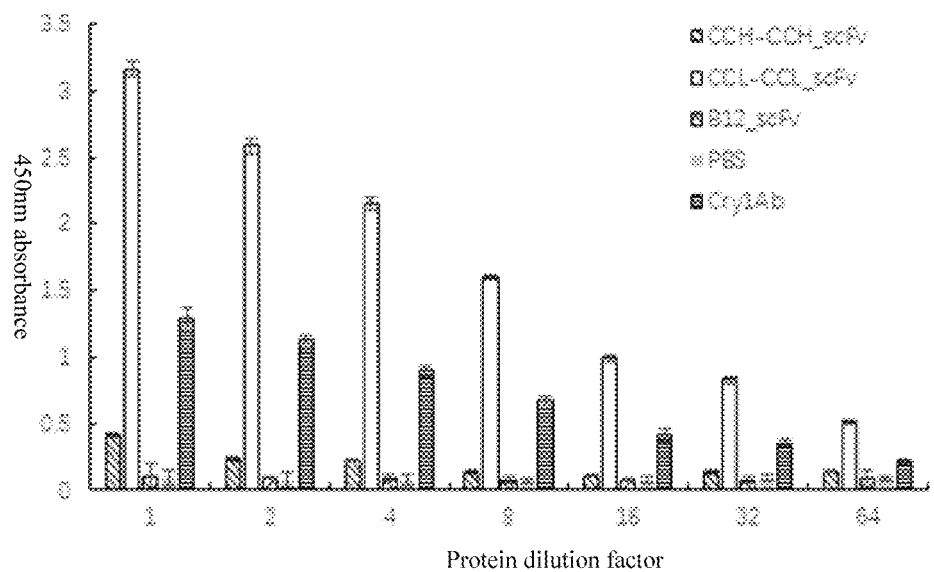
FIG. 5B

SEQUENCE LISTING

```
<160> NUMBER OF SEQ ID NOS: 7

<210> SEQ ID NO 1
<211> LENGTH: 237
<212> TYPE: PRT
<213> ORGANISM: artificial sequence
<220> FEATURE:
<223> OTHER INFORMATION: A human-derived molecularly modified
      insecticidal protein

<400> SEQUENCE: 1

Met Ala Thr Asp Ile Gln Met Thr Gln Ser Pro Ser Ser Leu Ser Ala
1               5                   10                  15

Ser Val Gly Asp Arg Val Thr Ile Thr Cys Arg Ala Ser Gln Ser Ile
            20                  25                  30

Ser Ser Tyr Leu Asn Trp Tyr Gln Gln Lys Pro Gly Lys Ala Pro Lys
        35                  40                  45

Leu Leu Ile Tyr Ala Ala Ser Arg Leu Gln Ser Gly Val Pro Ser Arg
    50                  55                  60

Phe Ser Gly Ser Gly Ser Gly Thr Asp Phe Thr Leu Thr Ile Ser Ser
65                  70                  75                  80

Leu Gln Pro Glu Asp Phe Ala Thr Tyr Tyr Cys Gln Gln Thr Ser His
                85                  90                  95

Pro Pro Leu Thr Phe Gly Gln Gly Thr Lys Val Glu Ile Lys Arg Ser
            100                 105                 110

Ser Gly Gly Gly Gly Ser Gly Gly Gly Ser Gly Gly Gly Gly Ser
        115                 120                 125

Thr Asp Ile Gln Met Thr Gln Ser Pro Ser Ser Leu Ser Ala Ser Val
    130                 135                 140

Gly Asp Arg Val Thr Ile Thr Cys Arg Ala Ser Gln Ser Ile Ser Ser
145                 150                 155                 160

Tyr Leu Asn Trp Tyr Gln Gln Lys Pro Gly Lys Ala Pro Lys Leu Leu
                165                 170                 175

Ile Tyr Ala Ala Ser Arg Leu Gln Ser Gly Val Pro Ser Arg Phe Ser
            180                 185                 190

Gly Ser Gly Ser Gly Thr Asp Phe Thr Leu Thr Ile Ser Ser Leu Gln
        195                 200                 205

Pro Glu Asp Phe Ala Thr Tyr Tyr Cys Gln Gln Thr Ser His Pro Pro
    210                 215                 220

Leu Thr Phe Gly Gln Gly Thr Lys Val Glu Ile Lys Arg
225                 230                 235
```

```
<210> SEQ ID NO 2
<211> LENGTH: 711
<212> TYPE: DNA
<213> ORGANISM: artificial sequence
<220> FEATURE:
<223> OTHER INFORMATION: A gene encoding a human-derived molecularly
      modified insecticidal protein

<400> SEQUENCE: 2
atggccacgg acatccagat gacccagtct ccatcctccc tgtctgcatc tgtaggagac      60
agagtcacca tcacttgccg ggcaagtcag agcattagca gctatttaaa ttggtatcag     120
cagaaaccag ggaaagcccc taagctcctg atctatgctg catcccggtt gcaaagtggg     180
gtcccatcaa ggttcagtgg cagtggatct gggacagatt tcactctcac catcagcagt     240
ctgcaacctg aagattttgc aacttactac tgtcaacaga cttctcatcc tcctctgacg     300
ttcggccaag gaccaaggt ggaaatcaaa cggtcgagcg gtggaggcgg ttcaggcgga     360
ggtggcagcg gcggtggcgg gtcgacggac atccagatga cccagtctcc atcctccctg     420
tctgcatctg taggagacag agtcaccatc acttgccggg caagtcagag cattagcagc     480
tatttaaatt ggtatcagca gaaaccaggg aaagccccta agctcctgat ctatgctgca     540
tcccggttgc aaagtggggt cccatcaagg ttcagtggca gtggatctgg gacagatttc     600
actctcacca tcagcagtct gcaacctgaa gattttgcaa cttactactg tcaacagact     660
tctcatcctc ctctgacgtt cggccaaggg accaaggtgg aaatcaaacg g              711

<210> SEQ ID NO 3
<211> LENGTH: 711
<212> TYPE: DNA
<213> ORGANISM: artificial sequence
<220> FEATURE:
<223> OTHER INFORMATION: a gene obtained through codon optimization

<400> SEQUENCE: 3
atggccaccg acatccagat gacccaaagc ccgagcagcc tgagcgcgag cgtgggtgac      60
cgtgttacca ttacctgccg tgcgagccag agcatcagca gctacctgaa ctggtatcag     120
caaaagccgg gtaaagcgcc gaagctgctg atttacgcgg cgagccgtct gcaaagcggc     180
gtgccgagcc gtttcagcgg tagcggtagc ggtaccgatt ttaccctgac catcagcagc     240
ctgcagccgg aggacttcgc gacctactat tgccagcaaa ccagccaccc gccgctgacc     300
tttggccaag gtaccaaggt tgaaattaaa cgttctagcg gtggcggtgg cagcggtggc     360
ggtggcagcg gtggcggtgg cagcaccgat attcaaatga cccagtctcc ttcttcttta     420
tctgcgagcg tgggtgaccg tgtaaccatc acctgccgcg cgagccaaag cattagcagc     480
tatctgaatt ggtatcagca aaaaccgggc aaggcgccga aactgctgat ctatgcggcg     540
agccgtctgc agagcggcgt gccgagccgc tttagcggca gcggcagcgg caccgacttc     600
accctgacca ttagcagcct gcaaccggaa gactttgcga cctactattg ccaacagacc     660
agccatccgc cgctgacctt cggccagggc accaaagtgg aaatcaaacg c              711

<210> SEQ ID NO 4
<211> LENGTH: 9
<212> TYPE: PRT
<213> ORGANISM: Homo sapiens

<400> SEQUENCE: 4

Cys Arg Ala Ser Gln Ser Ile Ser Ser
1               5
```

```
<210> SEQ ID NO 5
<211> LENGTH: 9
<212> TYPE: PRT
<213> ORGANISM: Homo sapiens

<400> SEQUENCE: 5

Lys Leu Leu Ile Tyr Ala Ala Ser Arg
1               5

<210> SEQ ID NO 6
<211> LENGTH: 15
<212> TYPE: PRT
<213> ORGANISM: artificial sequence
<220> FEATURE:
<223> OTHER INFORMATION: GS-linker

<400> SEQUENCE: 6

Gly Gly Gly Gly Ser Gly Gly Gly Gly Ser Gly Gly Gly Gly Ser
1               5                   10                  15

<210> SEQ ID NO 7
<211> LENGTH: 109
<212> TYPE: PRT
<213> ORGANISM: Homo sapiens

<400> SEQUENCE: 7

Thr Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
                20                  25                  30

Tyr Leu Asn Trp Tyr Gln Gln Lys Pro Gly Lys Ala Pro Lys Leu Leu
            35                  40                  45

Ile Tyr Ala Ala Ser Arg Leu Gln Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Thr Ser His Pro Pro
                85                  90                  95

Leu Thr Phe Gly Gln Gly Thr Lys Val Glu Ile Lys Arg
            100                 105
```

HUMAN-DERIVED INSECTICIDAL BT CRY TOXIN MIMETIC, AND DESIGN METHOD AND APPLICATION THEREOF

CROSS-REFERENCE TO RELATED APPLICATIONS

This application claims priority to Chinese application number 201810903129.1, filed Aug. 9, 2018 with a title of Improved Human-Derived Insecticidal Bt Cry Toxin Mimetic, and Design Method and Application Thereof. The above-mentioned patent application is incorporated herein by reference in its entirety.

TECHNICAL FIELD

The present invention relates to the field of genetic engineering and biological control, and in particular to a human-derived molecularly modified insecticidal protein, encoding gene, and design method and application thereof.

BACKGROUND

*Bacillus thuringiensis* (Bt) is an insect pathogenic bacteria, and the main insecticidal active substance thereof is an intracellular toxin, parasporal crystal protein, which has a specific poisonous effect for many agricultural pests (Bravo and Soberon, 2008); Cry1Ac is one of Bt toxins, and its target receptors for lepidoptera insects mainly include: alkaline phosphatase (ALP), aminopeptidase N (APN), and cadherin on rush border membrane vesicles (BBMV). As the receptor of Cry1A toxin, the ALP can promote the insertion of the toxin into membrane and the formation of a pore. Many ALPs isolated from species of diptera and lepidoptera insects have been identified as the receptor of Cry1Ac toxin. An anti-Cry1Ac toxin idiotypic single-chain antibody fragment (Anti-idiotype antibody scFvs, Anti-Id scFvs) can simulate the structure and function of Cry1Ac toxin.

An increased amount of Bt toxin has the ecological risks of pest resistance to insecticide and secondary pest rise (Bravo and Soberon, 2008; Pigott et al., 2008). This situation promotes the active development of Bt toxin resources resistant to pests having high specific activity and new function class. Since Cry1Ab toxin anti-Id scFv can simulate Cry1Ab toxin and compete with it for receptor proteins, the antibody has become a worldwide focus of scientific research. Chinese patent No. ZL201410037000.9 (U.S. Pat. No. 9,751,952 B2) disclosed a human-derived insect-resistant gene and Cry1Ab toxin Anti-Id scFv B12 encoded thereby (hereinafter referred to as B12), which can simulate Bt toxin and is used as a biopesticide for pest control, and has a positive effect. However, the soluble expressed protein of B12 antibody cannot bind to insectival BBMV, so the insecticidal efficacy is not ideal.

Genetic engineering, also known as the gene splicing technology and recombinant DNA technology, is based on molecular genetics in theory, and by means of the modern methods of molecular biology and microbiology. According to the predesigned map, with respect to genes from different sources, the DNA molecules are artificially "sheared" and "spliced", the biological genes are modified and recombinated, the recombinant DNA molecules are constructed in vitro, then is transformed into living cells, so the gene product needed by human is generated. For example, in 2002, DeMaagd discovered that with respect to Cry1Ab, when replaced domain III of Cry1C toxin, the toxicity for asparagus caterpillar is raised around 10 times as compare with Cry1C.

As the knowledge of the relationship between structure and function of antibodies is deepening continuously, the antibody gene modification by computer analog technology can design antibodies on purpose within a defined scope. According to amino acid site analysis of antigen-antibody binding, the antibody is designed and engineered in a directional mode. Wong et al. (1995) mutated Phe at position 108 of anti-p-azophenylarsonate Fab into Trp based on known three-dimensional structure of antigen-antibody complex, the mutation affinity is raised 10 times as compare with the wild type antibody; this indicates the direction for further engineering the binding region of an antibody molecule. However, at present, a method for improving the affinity of anti-Bt toxin idiotypic single-chain single-chain antibody in combination with the molecular modification method of chain shuffling and passing through the screening on Octet technology platform has not been reported.

SUMMARY

With regard to the above problems, the present invention provides a human-derived molecularly modified insecticidal protein, encoding gene, and design method and application thereof. The human-derived molecularly modified insecticidal protein shows significantly higher affinity with midgut BBMV of *Plutella xylostella* than Cry1Ab toxin, competes with Cry1Ab and Cry1Ac toxins for binding the midgut BBMV of *Plutella xylostella*, and is a mimic of Cry1Ab and Cry1Ac toxins, effectively replacing Cry1Ac toxin for biological control of insect pests, and having an insecticidal effect.

The present invention provides a human-derived molecularly modified insecticidal protein CCL-CCL_scFv, and the amino acid sequence of the insecticidal protein is shown as SEQ ID No. 1.

The present invention provides a method for designing the above human-derived molecularly modified insecticidal protein CCL-CCL_scFv, includes the following steps:

1) performing BLAST alignment analysis on the amino acid sequences of anti-Cry1Ab toxin idiotypic single-chain antibody (Cry1Ab anti-Id scFv) B12_scFv and Cry1A type toxins, to obtain similar sequences of B12_scFv and Cry1A type toxins, which respectively are H-CDR 1, L-CDR1, L-CDR2 and GS-linker;

2) connecting two light chain regions (VL) containing L-CDR1 and L-CDR2 head to tail with the GS-linker, to obtain human-derived molecularly modified insecticidal protein CCL-CCL_scFv.

The present invention provides an insecticide, including the above human-derived molecularly modified insecticidal protein, or a human-derived molecularly modified insecticidal protein designed by the above method.

The present invention provides a gene encoding human-derived molecularly modified insecticidal protein, and the gene includes: genes shown by (a) and (b):

(a) a gene consisting of the nucleotide sequence shown in SEQ ID No. 2;

(b) a gene obtained through codon optimization based on the nucleotide sequence defined by (a).

Preferably, the (b) gene consists of the nucleotide sequence shown in SEQ ID No. 3.

The present invention also provides a recombinant vector containing the above gene.

The present invention also provides an application of the above human-derived molecularly modified insecticidal protein, a human-derived molecularly modified insecticidal protein obtained by the above design method, the above insecticide, gene or recombinant vector in crop pest control.

Preferably, the pest includes *Plutella xylostella*.

Preferably, the crop includes Cruciferous crop.

Beneficial Effects:

(1) The present invention provides a human-derived molecularly modified insecticidal protein CCL-CCL_scFv, and the amino acid sequence of the human-derived molecularly modified insecticidal protein CCL-CCL_scFv is shown as SEQ ID No. 1. The human-derived molecularly modified insecticidal protein shows significantly higher affinity with midgut BBMV of *Plutella xylostella* than B12_scFv and Cry1Ab toxin, competes with Cry1Ab and Cry1Ac toxins for binding the midgut BBMV of *Plutella xylostella* heavier, and is a mimic of Cry1Ab and Cry1Ac toxins. Through *Plutella xylostella* indoor toxicity bioassay, the insecticidal protein shows a good insecticidal effect, and can effectively replace Cry1Ac or Cry1Ab toxin for biological control of insect pests.

Meanwhile, the human-derived molecularly modified insecticidal protein CCL-CCL_scFv provided by the present invention is obtained from modification and splicing of B12_scFv gene molecule. The antibody backbone is unchanged, and both the antibody and B12_scFv belong to human-derived antibody. Therefore, when applied to agricultural pest control, the insecticidal protein CCL-CCL_scFv shows small harm to human body.

(2) The present invention provides a method for designing the above human-derived molecularly modified insecticidal protein, including: performing BLAST alignment analysis on the amino acid sequences of the Cry1Ab anti-Id scFv B12_scFv and Cry1A type toxins, to obtain similar sequences of H-CDR 1, L-CDR 1, L-CDR2, and GS-linker of B12_scFv and Cry1A type toxins; connecting two light chain regions containing L-CDR1 and L-CDR2 sequences head to tail with the GS-linker, to obtain a human-derived molecularly modified insecticidal protein CCL-CCL_scFv. Compared with conventional antibody modification method (such as error-prone PCR etc.), the method provided by the present invention can prevent blindness with a higher success rate; and the method uses computer molecular simulation as the basis, predicts the binding domain among molecules and determines the key amino acid residues based on the information of known protein three-dimensional structure and function, and more accurately reflects the characteristics of antibody-protein interface, such that the molecular analog computation is more accurate, the prediction accuracy is greatly increased.

BRIEF DESCRIPTION OF THE DRAWINGS

FIGS. 2A-2E are three-dimensional structure diagrams of B12_scFv, modified CCL-CCL_scFv, CCH-CCH_scFv and Bt toxin Cry1Ab in Embodiment 3 of the present invention. More specifically, FIG. 2A is a three-dimensional structure diagram of B12_scFv (1f3r.1.B of scFv MAB198 as the template).

FIG. 2B is a three-dimensional structure diagram of CCL-CCL_scFv (the light chain region 4hjj.1.c of Anti-IL12 Anti-IL18 DFab as the template).

FIG. 2C is a three-dimensional structure diagram of CCH-CCH_scFv (5gs1.1.1 of bivalent bispecific antibody as the template).

FIG. 2D is a three-dimensional structure diagram of Cry1Ab (Cry1A(a) 1ciy as the template); and FIG. 2E is a three-dimensional structure diagram of PxALP (human 1zef.1.A as the template).

FIG. 3 shows a three-dimensional structure diagram of B12_scFv, is a three-dimensional structure diagram of CCL-CCL_scFv, is a three-dimensional structure diagram of CCH-CCH_scFv, is a three-dimensional structure diagram of Cry1Ab, is a three-dimensional structure diagram of PxALP (selecting human ALP 1zef.1.A as the template), is a three-dimensional structure diagram of the molecular docking between B12_scFv and PxALP, is a three-dimensional structure diagram of the molecular docking between CCL-CCL_scFv and PxALP, is a three-dimensional structure diagram of the molecular docking between CCH-CCH_scFv and PxALP, and is a three-dimensional structure diagram of the molecular docking between Cry1Ab and PxALP.

FIG. 4 is the analysis of binding hot spot in a complex after B12_scFv, modified CCL-CCL_scFv, CCH-CCH_scFv, and Bt toxin Cry1Ab in Embodiment 3 of the present invention bind with PxALP receptor respectively. More specifically, FIG. 4 respectively shows a three-dimensional structure diagram of binding hot spot of Cry1Ab, B12_scFv, CCL-CCL_scFv and CCH-CCH_scFv with ALP receptor binding region I, at right side of the figure, it is the main binding domain of the ligands and respectively are a three-dimensional structure diagram of binding hot spot of Cry1Ab, B12_scFv, CCL-CCL_scFv and CCH-CCH_scFv with ALP receptor binding region II, at left side of the figure, it is the main binding domain of the ligand.

FIGS. 5A and 5B show the binding activity assay and screening results of Cry1Ab, B12_scFv, CCL-CCL_scFv and CCH-CCH_scFv in Embodiment 4 of the present invention, where the assay uses the Bio-layer interferometry (BLI), ForteBio Octet Molecular interaction technology platform and ELISA, and adopts midgut brush-border membrane vesicle protein BBMV of *Plutella xylostella* as the target antigen. More specifically, FIG. 5A is the assay result of active insecticidal protein binding activity using Bio-layer interferometry (BLI), ForteBio Octet ForteBio Octet Molecular interaction technology platform; and FIG. 5B is the screening result of an insecticidal protein using ELISA.

FIG. 6A-6C show the assay results of affinity constant of Cry1Ab and CCL-CCL_scFv in Embodiment 4 of the present invention, where the assay uses the Bio-layer Interferometry (BLI), ForteBio Octet Molecular interaction technology platform and ELISA, and adopts midgut brush-border membrane vesicle protein BBMV of *Plutella xylostella* as the target antigen. More specifically, FIG. 6A is the binding Curve of CCL-CCL_scFv and *Plutella xylostella* BBMV at different dilute concentrations, FIG. 6B is the binding Curve of Bt toxin Cry1Ab and *Plutella xylostella* BBMV at different dilute concentrations and FIG. 6C is the affinity constant.

FIGS. 8A and 8B show the result of the Competitive inhibition experiment of CCL-CCL_scFv with Bt toxins Cry1Ab and Cry1Ac in Embodiment 6 of the present invention, where the experiment uses ELISA, using midgut brush-border membrane vesicle (BBMV) of *Plutella xylostella* as the target antigen. More specifically, FIG. 8A is the variation diagram of the ELISA absorbance of CCL-CCL_scFv competing with Bt toxins Cry1Ab and Cry1Ac for binding *Plutella xylostella* BBMV and FIG. 8B is the inhibition rate of CCL-CCL_scFv competing with Bt toxins Cry1Ab and Cry1Ac for binding *Plutella xylostella* BBMV.

DETAILED DESCRIPTION

Figure 1:
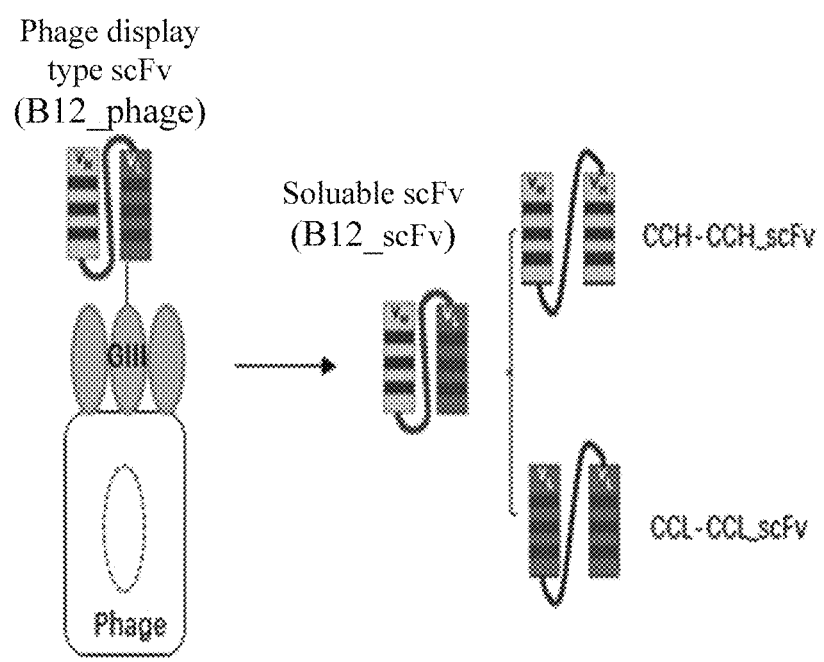
FIG. 1 is the design drawing of a human-derived molecularly modified insecticidal protein CCL-CCL_scFv of the present invention.

The present invention provides a human-derived molecularly modified insecticidal protein, and the amino acid sequence of the insecticidal protein is shown as SEQ ID No. 1.

In the present invention, the human-derived molecularly modified insecticidal protein is obtained by modification and splicing design of human-derived anti-Cry1Ab toxin idiotypic single-chain antibody (Cry1Ab anti-Id scFv) B12_phage molecule. The source of the single-chain antibody B12_phage sees Chinese patent No. ZL201410037000.9, entitled "human-derived insect-resistant gene and Cry1Ab anti-Id scFv encoded thereby and application thereof" and U.S. Pat. No. 9,751,952 B2. The B12_phage of the present invention is phage display type scFv, which is expressed in fusion with phage GIII protein. B12_scFv is soluble expressed scFv and does not have any phage structure. (The nucleic acid/protein) sequence of scFv portion in B12_phage is identical with the sequence of B12_scFv.

In the present invention, the method for designing the above human-derived molecularly modified insecticidal protein preferably includes the following steps:

1) performing BLAST alignment analysis on the amino acid sequences of Cry1Ab anti-Id scFv B12_scFv and Cry1A type toxins, to obtain similar sequences of B12_scFv and Cry1A type toxins, which respectively are H-CDR1, L-CDR1 (SEQ ID No. 4), L-CDR2 (SEQ ID No. 5) and GS-linker (SEQ ID No. 6);

2) connecting two light chain regions (VL) containing L-CDR1 and L-CDR2 sequences head to tail with the GS-linker, to obtain the amino acid sequence of the human-derived molecularly modified insecticidal protein CCL-CCL_scFv.

In the present invention, the nucleotide sequence of light chain regions (VL) containing L-CDR1 and L-CDR2 sequences as shown in SEQ ID No. 7.

The human-derived molecularly modified insecticidal protein CCL-CCL_scFv provided by the present invention is a mimetic of Cry1Ab and Cry1Ac toxins, which can compete with Bt toxins Cry1Ab and Cry1Ac for binding to *Plutella xylostella* BBMV, and the affinity of the human-derived molecularly modified insecticidal protein to *Plutella xylostella* BBMV is significantly higher than that of B12_scFv and Cry1Ab toxins.

The present invention provides a gene encoding human-derived molecularly modified insecticidal protein, the gene includes: genes shown by (a) and (b):

(a) a gene consisting of the nucleotide sequence shown in SEQ ID No. 2;

(b) a gene obtained through codon optimization based on the nucleotide sequence defined by (a).

In the present invention, the nucleotide sequence encoding gene (a) is obtained from molecular modification and splicing design of human-derived Cry1Ab anti-Id scFv B12_phage gene, and is artificially synthesized by Nanjing Ruizhen Biological Technology Co., Ltd. The nucleotide sequence encoding gene (b) is obtained through codon optimization based on the nucleotide sequence defined by (a). In the present invention, the codon optimization uses codon usage database which is available at the Kazusa Codon Usage Database (www.kazusa.or.jp/codon/), and CCL-CCL_scFv is optimized according to the Codon Usage Preference of *Escherichia coli*. In the present invention, the nucleotide sequence encoding gene (b) preferably consists of the nucleotide sequence shown in SEQ ID No. 3.

In the present invention, the method for preparing the human-derived molecularly modified insecticidal protein preferably uses the recombinant expression method. The method for preparing the human-derived molecularly modified insecticidal protein using the recombinant expression method includes the following steps:

(1) performing double enzyme digestion on the gene encoding the human-derived molecularly modified insecticidal protein and vector, then ligating to form a recombinant vector;

(2) transforming the recombinant vector into an expression cell system, performing induction culture to obtain the human-derived molecularly modified insecticidal protein.

In the present invention, the expression system preferably is a prokaryotic expression system. The prokaryotic expression system preferably is *Escherichia coli*. The *Escherichia coli* strain preferably is BL21(DE3). The vector preferably includes pET-26b, pET28a, more preferably is pET-26b. The double enzyme digestion preferably uses enzymes Nco I and Not I. The double enzyme digestion system is: 1 µl enzymes Nco I and Not I respectively, 43 µl vector, 5 µl 10× cutsmart buffer, 37° C. for 30 min. T4 ligation system is: 1 µl double enzyme digestion vector, 7 µl DNA fragment, 1 µl T4 ligase and 1 µl 10×T4 ligase reaction solution. In the embodiments of the present invention, the method for constructing the recombinant vector is: Adding a Nco I restriction site to N-terminal of the nucleic acid sequence of the human-derived molecularly modified insecticidal protein CCL-CCL_scFv, and adding a Not I restriction site to its C-terminal for synthesizing the gene, performing double enzyme digestion, then transforming the same into pET-26b vector.

The present invention provides an insecticide, including the above human-derived molecularly modified insecticidal protein, or the human-derived molecularly modified insecticidal protein CCL-CCL_scFv designed by above method.

In the present invention, the mass content of the human-derived molecularly modified insecticidal protein CCL-CCL_scFv in the insecticide preferably is 0.1-99%, more preferably is 1-50%.

The present invention does not particularly limit the method for preparing the insecticide, and any conventional method in the art is acceptable, specifically, combining the human-derived molecularly modified insecticidal protein and an acceptable carrier in the art.

In the present invention, when the insecticide is used, the leaf-dip method, or feeding insect after the artificial diet is soaked and dried is preferred.

The present invention also provides an application of the above human-derived molecularly modified insecticidal protein CCL-CCL_scFv, insecticide, gene or recombinant vector in crop pest control.

In the present invention, the application in crop pest control includes any method for preparing the insecticidal protein of the present invention for the purpose of crop pest control, method for preparing the gene encoding the insecticidal protein of the present invention, method for preparing the insecticidal recombinant bacteria of the present invention, method for preparing the insecticide of the present invention, and method for administrating the insecticidal protein, insecticide and insecticidal recombinant bacteria to crop area.

In the present invention, preferably, the crop pest includes *Plutella xylostella*, and preferably, the crop includes Cruciferous crops, more preferably, the crop is Chinese cabbage.

The human-derived molecularly modified insecticidal protein CCL-CCL_scFv of the present invention is obtained from modification and splicing of B12_scFv gene molecule. The antibody backbone is unchanged, and both the antibody and B12_scFv belong to human-derived antibody. Therefore, when applied to agricultural pest control, the insecticidal protein CCL-CCL_scFv shows small harm to human body.

After the human-derived molecularly modified insecticidal protein CCL-CCL_scFv is prepared, the present invention dilutes B12_scFv, CCL-CCL_scFv, CCH-CCH_scFv and Bt toxin Cry1Ab protein with PBS to a specified concentration, takes 500 μL diluents respectively for plating on the diet surface in the petri dish, then is air dried; the negative control is PBS buffer, and the positive control is Bt toxin protein.

30 second-instar *Plutella xylostella* larvae which have fasted for 4 h are inoculated into each diet petri dish, then are placed into an incubator at 25±1° C., of which the relative humidity is 80±5% and illumination condition is greater 14 h for feeding. After 3 d and 7 d, the number of dead insects is observed and recorded. When the larvae are taken out for examination, using a small brush to contact the body gently, the insect having no obvious reaction is dead. When assessed 7 d later, larvae that were dead or did not grow to the pupa were considered dead. Each treatment is repeated 3 times. The mortality of experimental insects is corrected by Abbott formula, and is represented by mean±standard error (3 repeated experiments).

Corrected mortality=(mortality of treatments-control mortality)/(1-control mortality)×100%.

When each treatment has the same time, the comparison of each sample uses One-way ANOVA and Tukey significance test, uses SPSS software for data processing, and the processing result shows that: After 3 days, the corrected *Plutella xylostella* larval mortality of CCL-CCL_scFv is 55.35%, and the corrected mortality of B12_scFv is lower than 10%. After 3 days, the corrected mortality of CCL-CCL_scFv is about 5 times higher than that of B12_scFv. After 7 d, the corrected mortality of CCL-CCL_scFv on *Plutella xylostella* is 85%. It could be seen that CCL-CCL_scFv has a good insecticidal effect.

As the concentrations of Bt toxins increasing, the binding activity of CCL-CCL_scFv with *Plutella xylostella* BBMV is Inhibited. CCL-CCL_scFv is a mimic of Cry1Ab and Cry1Ac toxins. The result demonstrates that the human-derived molecularly modified insecticidal protein provided by the present invention can effectively replace Cry1Ac or Cry1Ab toxin for biological control of insect pests.

A human-derived molecularly modified insecticidal protein, encoding gene, preparation method and application thereof according to the present invention will be further described in detail with reference to specific embodiments. The technical solutions of the present invention include, but are not limited to, the following embodiments.

The experimental material related to the embodiments:
vector pET26b: purchased from Novagene, Germany; all enzymes Nco I, Not I, T4 DNA ligase from NEB;
PCR reagentsfrom TransGen Biotech;
plasmid extraction kit, PCR product purification kit, PCR product gel recovery kit from Axygen;
Competent *Escherichia coli* BL21 (DE3) from TransGen Biotech;
HRP Conjugated Anti-Histag Mouse Monoclonal Antibody and HRP Conjugate Goat Anti-rabbit IgG from GE;
Cry1Ab and Cry1Ac toxins from Shanghai Youlong Biotech Co., Ltd;
96-well plate (Costar 3599) from Corning, USA.

Embodiment 1

A method for designing and preparing a human-derived molecularly modified insecticidal protein, and the specific steps are as follows:

(1) performing BLAST alignment analysis on the amino acid sequences of Cry1Ab anti-Id scFv B12_scFv and Cry1A type toxins (Cry1Aa, Cry1Ab, and Cry1Ac), analyzing the similar sequences of B12 as Cry1A type toxins, which respectively are H-CDR 1, L-CDR 1, L-CDR 2 and GS-linker.

(2) designing splicing according to the result, replacing the light chain region (VL) of Cry1Ab anti-Id scFv B12_scFv with the heavy chain region (VH), to obtain the double heavy chain antibody CCH-CCH_scFv; replacing the heavy chain region (VH) of Cry1Ab anti-Id scFv B12_scFv with the light chain region (VL), to obtain the double light chain antibody CCL-CCL_scFv, and performing BLAST alignment analysis again.

(3) performing homologous modeling on the amino acid sequences of the Cry1Ab anti-Id scFv B12_scFv, human-derived molecularly modified protein CCL-CCL_scFv and CCH-CCH_scFv, Cry1Ab toxin and ALP on midgut BBMV of *Plutella xylostella* respectively: the Cry1Ab anti-Id scFv B12_scFv selects 1f3r.1.B of scFv MAB198 as the template for homologous modeling, the human-derived molecularly modified protein CCH-CCH_scFv selects 5gs1.1.1 of a bivalent bispecific antibody as the template for homologous modeling, the human-derived molecularly modified protein CCL-CCL_scFv selects the light chain region 4hjj.1.c of Anti-IL12 Anti-IL18 DFab as the template for homologous modeling, Cry1Ab toxin selects Cry1A(a) 1ciy as the template for homologous modeling, and PxALP selects human ALP 1zef.1.A as the template for homologous modeling.

(4) performing molecular docking of the homologous modeling of the Cry1Ab anti-Id scFv B12_scFv, CCL-CCL_scFv, CCH-CCH_scFv, Cry1Ab toxin and ALP from midgut BBMV of *Plutella xylostella* using ZDOCK program, submitting the docking complex to Mitchell Lab hot spot prediction server KFC2, defining B12_scFv, CCL-CCL_scFv, CCH-CCH_scFv, and Cry1Ab toxin as the ligands, performing analysis on the ligand hot spot in binding domain to PxALP which is the same as Cry1Ab.

(5) obtaining the nucleic acid sequences of CCL-CCL_scFv and CCH-CCH_scFv by adding a Nco I restriction site to N-terminal, adding a Not I restriction site to its C-terminal and synthesizing the gene, then transforming into pET-26b vector, using *Escherichia coli* BL21 (DE3) for expression, where the target protein is purified by GE His-trap affinity column.

(6) using Bio-layer interferometry, ForteBio Octet Molecular interaction technology platform and ELISA, and using midgut brush-border membrane vesicle (BBMV) of

*Plutella xylostella* as the target antigen, screening out a human-derived molecularly modified protein CCL-CCL_scFv having a high BBMV binding activity, and determining the affinity constant.

(7) using ELISA, and using midgut brush-border membrane vesicle (BBMV) of *Plutella xylostella* as the target antigen, performing competitive inhibition experiment on human-derived molecularly modified proteins CCL-CCL_scFv, Cry1Ab and Cry1Ac, to verify the characteristic CCL-CCL_scFv simulating Cry1A type toxins.

(8) performing *Escherichia coli* codon optimization on the amino acid sequence of the human-derived molecularly modified protein, where the amino acid sequence (a) of CCL-CCL_scFv is optimized to CCL-CCL_scFv (b).

Embodiment 2

BLAST alignment analysis is performed on the amino acid sequences of Cry1Ab anti-Id scFv B12_scFv, modified CCL-CCL_scFv, CCH-CCH_scFv, and Cry1A type toxins (Cry1Aa, Cry1Ab, and Cry1Ac):

The amino acid sequence of Cry1Ab anti-Id scFv B12 (hereinafter referred to as B12_phage, from phage vector pIT2, being a phage display type single chain antibody (scFv), and a scFv co-expressed on GIII protein of phage ghost, as shown in left side of FIG. 1) has been disclosed by Chinese patent ZL201410037000.9 and U.S. Pat. No. 9,751,952 B2. B12_scFv is the antibody sequence from B12_phage, and is recombinated to prokaryotic expression vector pET-26b, is a soluble expressed scFv, and is shown in the middle part of FIG. 1.

The amino acid sequences of Bt toxins Cry1Aa, Cry1Ab and Cry1Ac are obtained from NCBI Protein database, the accession numbers are: AFK79795.1, ALJ10947.1 and ALT07695.1.

B12_scFv amino acid sequences are submitted to BLAST website which is available at the Basic Local Alignment Service Tool provided by the U.S. National Institute of Health and the U.S. National Library of Medicine (https://blast.ncbi.nlm.nih.gov/Blast.cgi), and alignment is performed with the amino acid sequences of Cry1Aa, Cry1Ab and Cry1Ac respectively. The alignment result is shown in table 1.

TABLE 1

Blast analysis result

| Recombinat proteins | Similar regions of recombinant proteins | Similar regions of Cry1A type proteins |
|---|---|---|
| B12_scFv | H-CDR 1 | Endotoxin_N terminal domain |
|  | L-CDR 1 & CDR 2 | Endotoxin_C terminal domain |
|  | GS-linker | Endotoxin_C terminal domain (domain III) |
| CCL-CCL_scFv | L-CDR 1& CDR 2 | Endotoxin_C terminal domain |
|  | GS-linker | Endotoxin_C terminal domain |
| CCH-CCH_scFv | H-CDR 1 | Endotoxin_N terminal domain |
|  | GS-linker | Endotoxin_C terminal domain |

H-CDR1 region of the heavy chain of B12_scFv and the conserved domain, Endotoxin_N terminal domain of Cry1A type protein have a similar sequence. Endotoxin_N terminal domain mainly is the N terminal structure of Bt insecticidal toxin. N-terminal helix domain relates to membrane insertion and pore formation, so speculates H-CDR1 region of the heavy chain of B12_scFv may has a similar function. L-CDR 1 and L-CDR 2 regions of light chain of B12_scFv and the conserved domain, Endotoxin_C terminal domain of Cry1A type protein have a similar sequence. Endotoxin_C terminal domain mainly is the C terminal structure of Bt insecticidal toxin, and mainly relates to receptor binding. Thus, it is supposed that the heavy chain region of B12_scFv mainly is an insecticidal active region, and the light chain region of B12_scFv mainly is a binding active region.

According to the Blast analysis result, in order to increase the binding activity of B12_scFv, replacing the light chain region (VL) of Cry1Ab anti-Id scFv B12_scFv with the heavy chain region (VH), to obtain the double heavy chain antibody CCH-CCH_scFv, replacing the heavy chain region (VH) with the light chain region (VL), to obtain the double light chain antibody CCL-CCL_scFv (as shown in FIG. 1).

The amino acid sequences of modified CCL-CCL_scFv and CCH-CCH_scFv are submitted to BLAST Website, and alignment is performed with the amino acid sequences of Cry1Aa, Cry1Ab and Cry1Ac, the alignment result is shown in FIG. 1. L-CDR 1 and L-CDR 2 regions of light chain of CCL-CCL_scFv and the conserved domain, Endotoxin_C terminal domain of Cry1A type protein have a similar sequence, and H-CDR1 region of the heavy chain of CCH-CCH_scFv and the conserved domain, Endotoxin_N terminal domain of Cry1A type protein have a similar sequence.

Embodiment 3

Homologous modeling and molecular docking of B12_scFv, modified CCL-CCL_scFv, CCH-CCH_scF, Bt toxin Cry1Ab and alkaline phosphatase (ALP) of *Plutella xyllostella* (PxALP):

(1) Homologous Modeling

The amino acid sequence of B12_phage has been disclosed by Chinese patent ZL201410037000.9 and U.S. Pat. No. 9,751,952 B2. The amino acid sequence of PxALP is obtained from NCBI Protein database, and the accession number is: AHF20243.2. The amino acid sequence of Bt toxin Cry1Ab is obtained from NCBI Protein database, and the accession number is: ALJ10947.1.

The amino acid sequences of modified CCL-CCL_scFv and CCH-CCH_scFv are obtained by: according to the BLAST alignment analysis result of the amino acid sequences of B12_scFv and Cry1A type toxins (Cry1Aa, Cry1Ab, and Cry1Ac), replacing the light chain region (VL) of Cry1Ab anti-Id scFv B12_scFv with the heavy chain region (VH), and replacing the heavy chain region (VH) of Cry1Ab anti-Id scFv B12_scFv with the light chain region (VL) (as shown in FIG. 1).

The homologous modeling method of B12_scFv, Cry1Ab, modified CCL-CCL_scFv, CCH-CCH_scFv and PxALP is: using Swiss-model website which is available at the Swiss-Model Expasy webserver (www.swissmodel.expasy.org/), searching out a template having a relative high identity from PDB (Protein Data Bank, Brookhaven National Laboratory) and modeling; After respectively obtaining the three-dimensional structures, then using Verify 3D and ERRAT programs of SAVES website which is available at the University of California Los Angeles (services.mbi.ucla.edu/SAVES/) to score above three-dimensional structures, and evaluating the compatibility of the three-dimensional structures and primary sequence and the reliability thereof.

In particular are: B12_scFv selects 1f3r.1.B of scFv MAB198 as the template for homologous modeling, the amino acid sequence identity with the template is 87.28%, its three-dimensional structure is shown in FIG. 2A, CCL-CCL_scFv selects the light chain region 4hjj.1.c of Anti-IL12 Anti-IL18 DFab as the template, the amino acid sequence identity with the template is 67.41%, and its three-dimensional structure is as shown in FIG. 2B; CCH-CCH_scFv selects 5gs1.1.1 of a bivalent bispecific antibody as the template, the amino acid sequence identity with the template is 61.84%, and its three-dimensional structure is as shown in FIG. 2C; Cry1Ab selects Cry1A(a) 1ciy as the template, the amino acid sequence identity with the template is 89.46%, and its three-dimensional structure is shown in FIG. 2D; and PxALP selects human ALP 1zef.1.A as the template, the amino acid sequence identity with the template is 44.93%, and its three-dimensional structure is as shown in FIG. 2E.

The evaluation result of the three-dimensional structure model of homologous modeled B12_scFv, modified CCL-CCL_scFv, CCH-CCH_scFv, Bt toxin Cry1Ab and PxALP is as shown in table 2:

TABLE 2

Evaluation result of three-dimensional structure model
Evaluation of simulation structure

| Model | Verify 3D values (% residue > 0.2) | Errat values |
| --- | --- | --- |
| Cry1Ab | 96.36 | 96.422 |
| B12 | 97.91 | 64.623 |
| CCL-CCL | 92.67 | 92.386 |
| CCH-CCH | 88.1 | 84.332 |
| ALP | 80.46 | 89.398 |

For a good three-dimensional structure model, the ERRAT evaluation should higher than 50, and in Verify 3D evaluation, at least 80% amino acid residues should greater than 0.2. According to the evaluation result shown in table 2, the above 5 three-dimensional structures of homologous modeling are reasonable and credible.

In the step, the protein three-dimensional structure output is completed by using PyMOL software (The PyMOL Molecular Graphics System, DeLano Scientific, San Carlos, Calif., USA).

Figure 3:
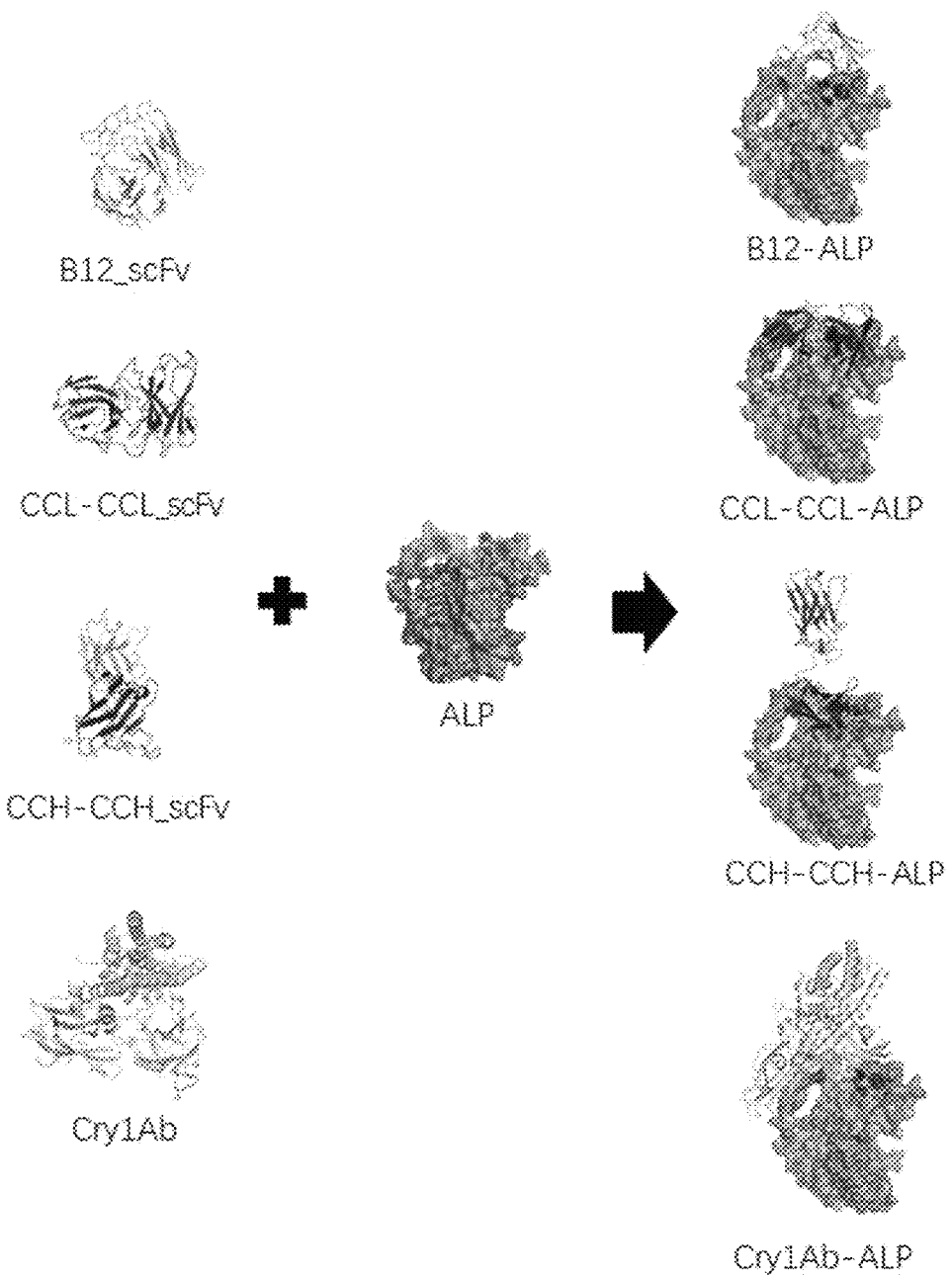
FIG. 3 is the schematic diagram of three-dimensional structural model of B12_scFv, modified CCL-CCL_scFv, CCH-CCH_scFv, Bt toxin Cry1Ab and PxALP in Embodiment 3 of the present invention when subjected to molecular docking.

(2) Molecular docking and hot spot prediction:

defining PxALP as the receptor, and Cry1Ab, B12_scFv, modified CCL-CCL_scFv and CCH-CCH_scFv as the ligands, using ZDOCK program which is available at The University of Massachusetts (zdock.umassmed.edu/), performing molecular docking on constructed PxALP model and 4 ligand model, firstly, with respect to Cry1Ab ligand, selecting first 10 predictive complexes, screening them according to known PxALP binding site, and performing the second determination by the PxALP receptor binding site on the Cry1Ab ligand; according to the Binding hot spot region of PxALP and Cry1Ab, screening the complexes of other 3 ligands (B12_scFv, CCL-CCL_scFv and CCH-CCH_scFv). The spatial structure diagram of the docking complexes of B12_scFv-PxALP, CCL-CCL_scFv-PxALP, CCH-CCH_scFv-PxALP and Cry1Ab-PxALP outputted by PyMOL software is shown on the right side of FIG. 3

Figure 4:
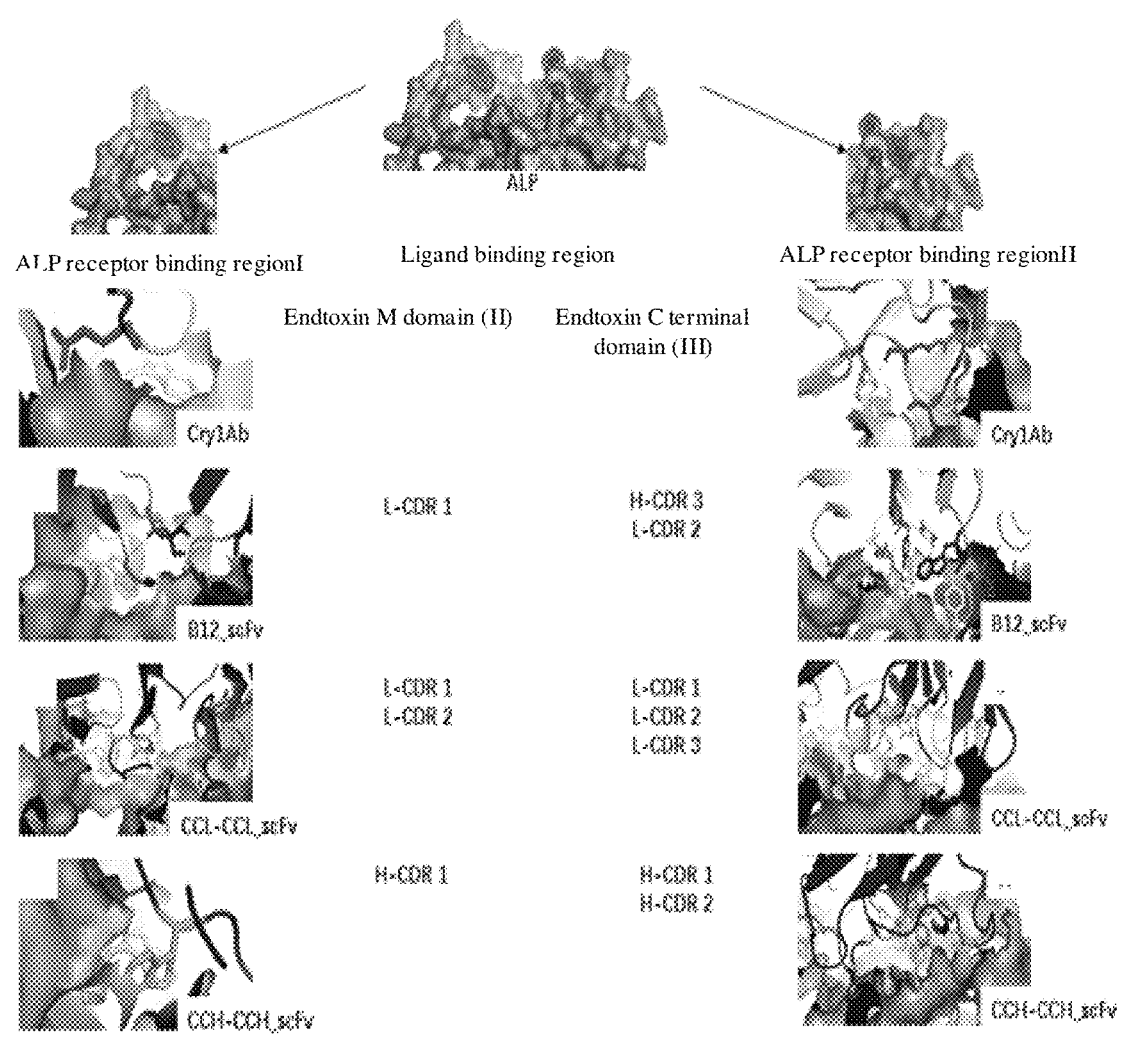

Submitting the above 4 docking complexes to the hot spot prediction server KFC2 Hot Spot Prediction Server which is available at The Oakridge National Laboratory Mitchell Server for a Macronuclear Interactions (kfc.mitchell-lab.org/) (Darnell et al.,2007), the prediction result is shown in FIG. 4, the hot spot prediction server KFC2 predicts that the consensus hot spot regions of PxALp receptor bound with 4 ligands is TRP53 (ALP receptor binding region I), ALA409, TYR411, and TYR433 (ALP receptor binding region II); The three-dimensional structure diagram of hot spot of 4 ligands bound with the receptor is as shown in FIG. 4, where the left side respectively shows a three-dimensional structure diagram of the binding hot spot of Cry1Ab, B12_scFv, CCL-CCL_scFv, CCH-CCH_scFv with ALP receptor binding region I, at right side of the figure, it is the main binding domain of the ligands; subfigures 4E, 4F, 4G and 4H respectively are a three-dimensional structure diagram of binding hot spot of Cry1Ab, B12_scFv, CCL-CCL_scFv and CCH-CCH_scFv with ALP receptor binding region II, at left side of the figure, it is the main binding domain of the ligands.

By comparison, B12_scFv binds PxALP receptor by hot spot amino acids in L-CDR 1 and 2 regions of the light chain and H-CDR 3 region of the heavy chain, modified CCL-CCL_scFv can bind PxALP receptor by hot spot amino acids in L-CDR 1 and 2 regions of the N-terminal light chain, and L-CDR 1, 2 and 3 regions of C-terminal light chain, and modified CCH-CCH_scFv can bind PxALP receptor by hot spot amino acids in H-CDR 1 region of the C-terminal heavy chain, and H-CDR 1 and 2 regions of C-terminal heavy chain. It can be seen from the result of the molecular docking simulation that the binding hot spot sites of modified CCL-CCL_scFv with PxALP receptor is increased compared with the parent B12_scFv. In addition to the same hot spot domains, L-CDR 1 and 2 regions of the light chain are the parent, predicts the binding capacity of CCL-CCL_scFv with ALP is stronger than that of B12_scFv, but the binding capacity of CCH-CCH_scFv is similar as that of B12_scFv, which is similar as the prediction result of earlier BLAST.

The programs related to the step are completed by PyMOL software and performing the image output by same.

Embodiment 4

Screening and Affinity Assay:

(1) Preparation of Midgut BBMV of *Plutella xylostella*

Making reference to the experimental method (Wolfersberger, 1987), using Mg-EGTA sedimentation method to prepare midgut BBMV of *Plutella xylostella*, the particular preparation method is: taking late fourth-stage larvae of *Plutella xylostella*, extracting the midguts, washing them in pre-cooled 0.15 M NaCl, adding 3 mL homogenization buffer to each 500 midguts; performing homogenization and ice bath repeatedly, adding equal volume of 24 mM $MgCl_2$, mixing it homogeneously, performing ice bath and low speed centrifugation, then transferring the supernatant to a new superspeed centrifugal tube, and performing superspeed centrifugation again; discarding the supernatant, then inverting the centrifugal tube to drain away the liquid, resuspending the precipitate in HEPES buffer, subpackaging the suspension and storing it at −80° C. for use; determining BBMV protein concentration by Bradford method.

(2) Screening Insecticidal Proteins by Bio-Layer Interferometry (BLI)

The experimental operation uses Octet Molecular interaction technology platform (ForteBio), and data analysis uses Data Analysis software (ForteBio). Materials used in the reaction process: all system buffer PBS (137 mM NaCl, 2.7 mM KCl, 10 mmol/L $Na_2HPO_4$, and 2 mM $KH_2PO_4$, pH 7.4), kinetic buffer (1×PBS buffer containing 0.1% (wt/vol) BSA) and Aminopropylsilane (APS) biosensor (Aminopropylsilane-coated biosensor tips) are the standard products of ForteBio.

Diluting the receptor protein midgut BBMV of *Plutella xylostella* used in the experiment to 10 μg/mL using PBS, and diluting B12_scFv, CCL-CCL_scFv, CCH-CCH_scFv and Bt toxin Cry1Ab to a specified concentration using kinetic buffer. All reagents are formulated using deionized water, and then are filtered by a 0.22 μm filter membrane.

Placing APS biosensor in PBS buffer and equilibrating it for 30 s, coating it with 10 μg/mL midgut BBMV of *Plutella xylostella* for 5 min, equilibrating and blocking APS biosensor using kinetic buffer for 1 min, meanwhile, placing it in expressed and purified B12_scFv, CCL-CCL_scFv, CCH-CCH_scFv and Bt toxin Cry1Ab for binding for 5 min, then placing it in BSA buffer, dissociating it for 5 min.

The result of real-time monitoring is as shown in FIG. 5A, the binding activity of CCL-CCL_scFv is the best, and is slow binding and slow dissociation, and the binding do not achieve the saturation state; The binding activity of Cry1Ab is relatively good, also is fast binding and slow dissociation, and the binding has achieved the saturation state; CCH-CCH_scFv binding is relatively poor, and is slow binding and fast dissociation; the binding effect of B12_scFv is relatively poor, and exhibit as fast binding and fast dissociation.

(3) Screening Insecticidal Proteins by ELISA

Taking 30 μg/mL midgut BBMV of *Plutella xylostella*, coating a 96 microwell plate at 100 μl/well, incubating it at 4° C. overnight, the next day, adding 200 μl 3% MPBS solution to each well, incubating it at 37° C. for 2 h to blocking it; washing the plate by using 250 μl PBST for each well, then adding expressed and purified B12_scFv, CCL-CCL_scFv, CCH-CCH_scFv and Bt toxin Cry1Ab (2 fold dilution gradient), 100 μl/well, incubating it at 37° C. for 2 h; washing the plate by using 250 μl PBST for each well, adding 1:5000 diluted HRP-Anti-Histag antibody (for Bt toxin Cry1Ab, it needs to add polyclonal antibody of Cry1Ab at 100 μl/well, incubating it at 37° C. for 1 h, washing the plate by using PBST, then adding HRP-goat anti rabbit IgG) at 100 μl/well, incubating it at 37° C. for 1 h; washing the plate by using PBST, then adding tetramethyl benzidine (TMB) solution at 100 μl/well, reacting it at 37° C. for 10-20 min, finally, adding 2 mol/L $H_2SO_4$ for stopping the reaction rapidly, and determining the OD450 value by a Thermo automatic microplate reader.

The result is as shown in FIG. 5B, in the gradiently-diluted samples, only CCL-CCL_scFv and Cry1Ab have binding activity, where the binding activity of CCL-CCL_scFv is the best, its OD450 value is up to at least 3.0.

(4) Affinity Assay of CCL-CCL_scFv and Cry1Ab by Bio-Layer Interferometry (BLI)

Diluting the receptor protein, midgut BBMV of *Plutella xylostella* to 10 μg/mL using PBS, and respectively diluting CCL-CCL_scFv and Bt toxin Cry1Ab using kinetic buffer to 4 μM, 2 μM, 1 μM and 0.5 μM.

Placing APS biosensor in PBS buffer and equilibrating it for 30 s, coating it with 10 μg/mL midgut BBMV of *Plutella xylostella* for 5 min, equilibrating and blocking APS biosensor using kinetic buffer for 1 min, meanwhile, placing it in the gradient diluent of purified CCL-CCL_scFv and Bt toxin Cry1Ab, binding them for 5 min, then placing it in kinetic buffer, dissociating it for 5 min.

Figures 6A, 6B, 6C:
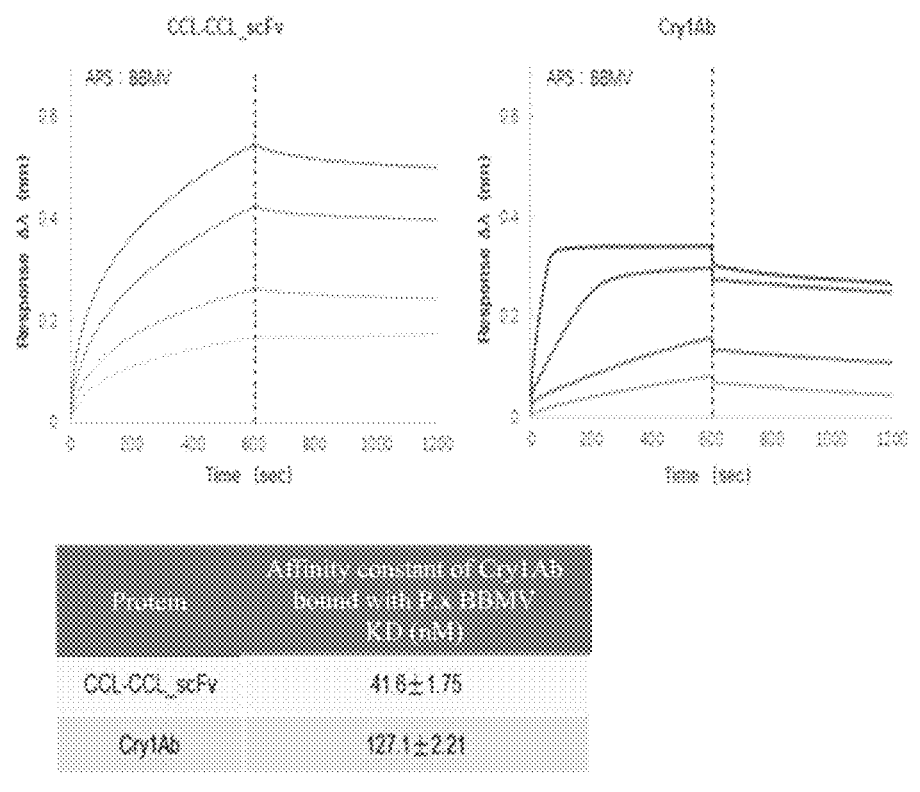

The result of real-time monitoring is as shown in FIG. 6A and FIG. 6B, where FIG. 6A is the binding curve of CCL-CCL_scFv with *Plutella xylostella* BBMV at different diluted concentrations, and FIG. 6B is the binding curve of Bt toxin Cry1Ab with *Plutella xylostella* BBMV at different diluted concentrations. The affinity is as shown in FIG. 6C, where the affinity of CCL-CCL_scFv with *Plutella xylostella* BBMV is 41.6±1.75 nM, and the affinity of Cry1Ab with *Plutella xylostella* BBMV is 127.1±2.21 nM.

In summary, at the same concentration, the BBMV binding activity of modified CCL-CCL_scFv is higher than that of Bt toxin Cry1Ab. Because of fast binding and fast dissociation (BLI real-time monitoring), in ELISA detection (endpoint detection method), B12_scFv do not exhibit binding activity. Screening proteins having BBMV binding activity using BLI technology, it save time and samples, and has a high throughput and can real-time monitor data, so it is easier than traditional ELISA method (10 hours). It is also more convenient, easier and faster than SPR method (BIA-core×100 experimental platform).

Embodiment 5

Toxicity Bioassay of Insecticidal Proteins

Dilutes B12_scFv, CCL-CCL_scFv, CCH-CCH_scFv and Bt toxin Cry1Ab protein with PBS to a specified concentration, takes 500 μL diluents respectively for plating on the artificial diet surface in the petri dish, then is air dried; the negative control is PBS buffer, and the positive control is Bt toxin protein.

30 second-instar *Plutella xylostella* larvae which have fasted for 4 h are inoculated into each artificial diet petri dish, and then are placed into an incubator at 25±1° ° C., of which the relative humidity is 80±5% and illumination condition is greater 14 h for feeding. After 3 d and 7 d, the number of dead insects is observed and recorded. When the larvae are taken out for examination, using a small brush to contact the body gently, the insect having no obvious reaction is dead. When assessed 7 d later, larvae that were dead or did not grow to the pupa were considered dead. Each treatment is repeated 3 times. The mortality of experimental insects is corrected by Abbott formula, and is represented by mean±standard error (3 repeated experiments).

Corrected mortality=(mortality of treatments−control mortality)/(1−control mortality)×100%

Figure 7:
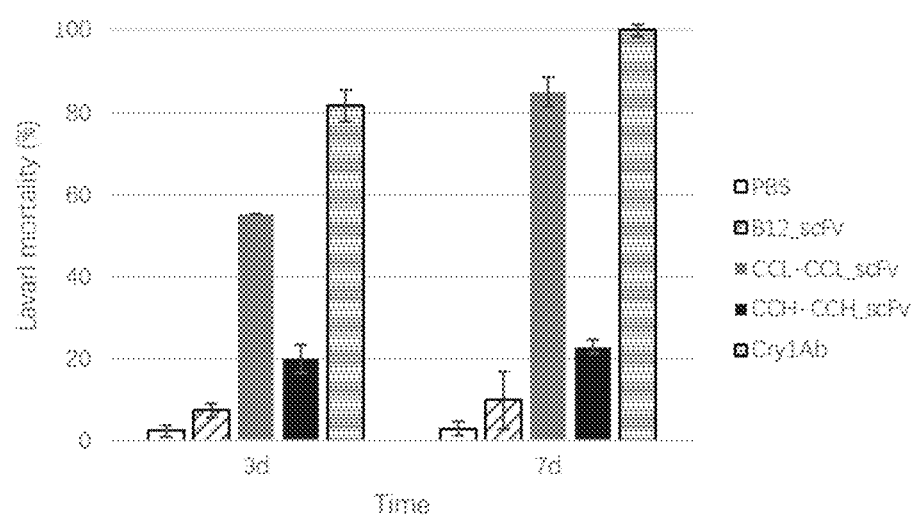
FIG. 7 shows the toxicity bioassay result in Embodiment 5 of the present invention, where the assay uses second-instar *Plutella xylostella* larvae as the experimental insect and adopts expressed and purified B12_scFv, CCL-CCL_scFv, CCH-CCH_scFv and Bt toxin Cry1Ab for test.

When each treatment has the same time, the comparison of each sample uses One-way ANOVA and Tukey significance test, uses SPSS software for data processing, and the processing result is shown in FIG. 7.

The assay result shows that after 3 days, the corrected mortality of CCL-CCL_scFv on *Plutella xylostella* is 55.35%, and the corrected mortality of B12_scFv is lower than 10% after 3 d, the corrected mortality of CCL-CCL_scFv is about 5 times higher than that of B12_scFv. After 7 d, the corrected mortality of CCL-CCL_scFv on *Plutella xylostella* is 85%. It could be seen that CCL-CCL_scFv has a good insecticidal effect.

Embodiment 6

The Competitive Inhibition Experiment of CCL-CCL_scFv with Bt Toxins by Using ELISA Using midgut brush-border membrane vesicle protein BBMV of *Plutella xylostella* as the target antigen, performing a competitive inhibition experiment on CCL-CCL_scFv with Bt toxins Cry1Ab and Cry1Ac.

Two times diluting Bt toxins Cry1Ab (40 mg/mL) and Cry1Ac (55 mg/mL) by using PBS. Mixing diluted Cry1Ab or Cry1Ac proteins with equal volume of CCL-CCL_scFv protein homogeneously, incubating it at 37° C. for 2 h.

Taking 30 μg/mL midgut BBMV of *Plutella xylostella*, coating a 96 microwell plate at 100 μl/well overnight, the next day, adding 200 μl 3% MPBS solution to each well, incubating it at 37° C. for 2 h to blocking it; washing the plate by using 250 μl PBST/well, then adding a series of CCL-CCL_scFv+Cry1Ab mixtures and CCL-CCL_scFv+Cry1Ac mixtures at 100 μl/well, incubating it at 37° C. for 2 h; washing the plate by using 250 μl PBST/well, adding 1:5000 diluted HRP-Anti-Histag antibody, incubating it at 37° C. for 1 h; washing the plate by using PBST, then adding tetramethyl benzidine (TMB) developing solution at 100 μl/well, reacting it at 37° C. for 10-20 min, finally, adding 2 mol/L $H_2SO_4$ for stopping the reaction rapidly, and determining the OD450 value by a Thermo automatic microplate reader.

Figures 8A, 8B:
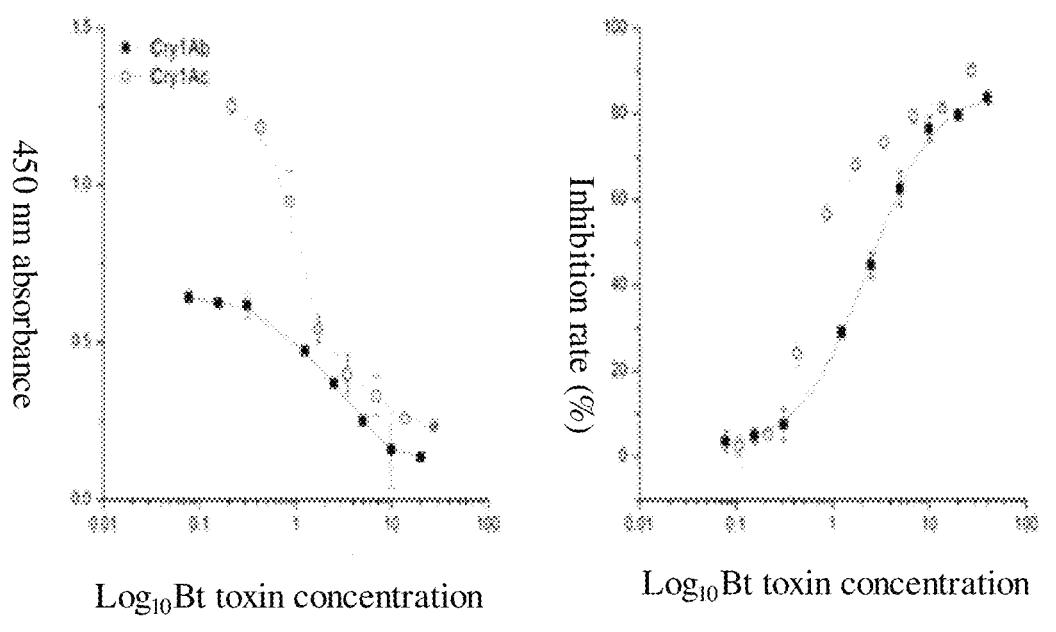

The ELISA result is as shown in FIG. 8A, as the concentrations of Bt toxins increasing, the binding activity of CCL-CCL_scFv with *Plutella xylostella* BBMV is Inhibited. The inhibition rate is as shown in FIG. 8B, where Cry1Ab binding *Plutella xylostella* BBMV results in the 50% inhibiting concentration ($IC_{50}$) on CCL-CCL_scFv is 3.02 μg/mL, and Cry1Ac binding *Plutella xylostella* BBMV results in the 50% inhibiting concentration ($IC_{50}$) on CCL-CCL_scFv is 1.7 μg/mL. Both Cry1Ab and Cry1Ac proteins can compete with CCL-CCL_scFv for binding *Plutella xylostella* BBMV, and the inhibition rate of CCL-CCL_scFv by Cry1Ac protein can achieve 90%. Therefore, it can determine that CCL-CCL_scFv is a mimic of Cry1Ab and Cry1Ac toxins, can be used to replacing Cry1Ac or Cry1Ab for biological control of insect pest.

The preferred embodiments of the present invention are described above, and it should be noted that for a person of ordinary skilled in the art, several improvements and modifications may further be made without departing from the principle of the present invention, and the improvements and modifications should also be considered to fall within the protection scope of the present invention.

What is claimed is:

1. A human-derived molecularly modified insecticidal protein, wherein the amino acid sequence of the human-derived molecularly modified insecticidal protein is shown as SEQ ID No. 1.

2. The method for designing the human-derived molecularly modified insecticidal protein according to claim 1, comprising the following steps:
   1) performing BLAST alignment analysis on the amino acid sequences of anti-Cry1Ab toxin idiotypic single-chain antibody (Cry1Ab anti-Id scFv) B12_scFv and Cry1A type toxins, to obtain similar sequences of B12_scFv and Cry1A type toxins, which respectively are H-CDR, L-CDR 1, L-CDR 2 and GS-linker;
   2) connecting two light chain regions containing L-CDR1 and L-CDR2 from B12 scFv head to tail with the GS-linker, to obtain a human-derived molecularly modified insecticidal protein CCL-CCL_scFv.

3. An insecticide comprising the human-derived molecularly modified insecticidal protein according to claim 1.

4. An insecticide comprising a human-derived molecularly modified insecticidal protein designed by the method according to claim 2.

* * * * *